(12) United States Patent
Shanbhag et al.

(10) Patent No.: US 12,174,821 B2
(45) Date of Patent: Dec. 24, 2024

(54) CURATION OF DATA FROM DISPARATE RECORDS

(71) Applicant: CERNER INNOVATION, INC., North Kansas City, MO (US)

(72) Inventors: Anand Parameshwar Shanbhag, Bangalore (IN); Srinidhi Kumble, Bangalore (IN); Sridhar Srinivasan, Tamil Nadu (IN)

(73) Assignee: Cerner Innovation, Inc., Kansas City, MO (US)

( * ) Notice: Subject to any disclaimer, the term of this patent is extended or adjusted under 35 U.S.C. 154(b) by 11 days.

(21) Appl. No.: 17/653,067

(22) Filed: Mar. 1, 2022

(65) Prior Publication Data

US 2023/0281183 A1   Sep. 7, 2023

(51) Int. Cl.
*G06F 16/23* (2019.01)
*G06F 16/22* (2019.01)
*G06F 16/28* (2019.01)
*G16H 10/60* (2018.01)

(52) U.S. Cl.
CPC ......... *G06F 16/2365* (2019.01); *G06F 16/22* (2019.01); *G06F 16/287* (2019.01); *G16H 10/60* (2018.01)

(58) Field of Classification Search
CPC .... G06F 16/2365; G06F 16/22; G06F 16/287; G16H 10/60
See application file for complete search history.

(56) References Cited

U.S. PATENT DOCUMENTS

| | | | |
|---|---|---|---|
| 2016/0300019 A1* | 10/2016 | Baluta | G06F 16/285 |
| 2016/0357915 A1* | 12/2016 | Morris | G16H 10/60 |
| 2020/0183950 A1* | 6/2020 | Gaillardetz | G06F 16/258 |
| 2021/0109915 A1* | 4/2021 | Godden | G16H 10/60 |
| 2022/0310276 A1* | 9/2022 | Wilkinson | G06Q 90/00 |

* cited by examiner

*Primary Examiner* — Jensen Hu
(74) *Attorney, Agent, or Firm* — Invoke (57) ABSTRACT

The boosting of the weights related to imperfect matches of electronic records from disparate sources is discussed. The imperfect matches may be in primary data (such as a code) and/or in supplemental data between two or more records that correspond to the same person (such as a patient). The imperfect matches are analyzed to determine whether they are sufficient to warrant de-duplication of those imperfect matches in a final combined record for the person. The boosting of the weights may be based upon any of numerous factors, such as various distance measures between the supplemental information as a measure of how different the supplemental information is between the respective records.

23 Claims, 8 Drawing Sheets

Today (10/22/21)

▼ 02:34 AM  ⊘ Emergency Department Consultation Note <Specialty 1> (Consultation Note)

Collected: 10/22/2021 02:34 AM

Encounter Information

Reason for Encounter Breathlessness.

HPI  Patient Stated Complaint [Breathless since 2 days.] Narrative of Presenting Problem [No fever, not cough, sweating, Onset 2 Days ago, Duration 2 Days, Timing Gradual, Occurred at Home, Context Currently Under Care for this Complaint Seen primary care.
                                            ─602                                                      ─604

Past History

Allergies
  • NKA
  • NKDA
  • NKFA

Medical and Surgical History    Medical None; Surgical None.

ROS

Review of System Note    [Weight gained is currently 100 kgs.]
                              ─606

▼ 02:00 AM  ⊘ Vital Signs

Collected: 10/22/2021 02:00 AM; Assessment Status: Complete

A_Pulse: 120 N
A_O2 Saturation (%): 96 N

CURATION OF DATA FROM DISPARATE RECORDS

BACKGROUND

Today's world is increasingly dependent on storing massive amounts of data. Big data in healthcare is an issue due to the abundant health data that is amassed from numerous sources including separate electronic health record (EHR) systems, EHRs, outpatient facilities, imaging facilities, databases, wearable devices, public records, patient portals, clinical studies, and the like. Health data is available in extraordinarily high volumes. Additionally, due to the numerous sources involved in the care of individuals, content of the sources is often times highly variable in structure and content. Prior art systems fail to curate these vast and disparate data collections. What is lacking in the prior art is a way to curate data sets from raw data collections.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description.

In brief and at a high level, this disclosure describes, among other things, methods, systems, and computer-readable media for curating data that is stored in response to a request for such data. The disclosure describes how a request may be interpreted and then electronic records accessed. Data from the electronic records may then be curated to meet the specific request, correct errors, draw conclusions, summarize findings, and perform other functions. Providers need tools that enable them to understand large amounts of disparate data that is typically stored in an disorganized or difficult to understand manner. Different systems inevitably use different standards or formats for their data, and the data entered contains errors and duplications. Thus, the systems described herein curate this data to more specifically and accurately meet the requests received.

A first embodiment of the invention is directed to a computerized method of providing curated data in response to a request. The method may include receiving, from a user device, a data request corresponding to a person. The method may further include acquiring, from a data store, a set of un-curated data associated with the person. The method may further include analyzing the set of un-curated data via an analysis engine to determine a data discrepancy. The method may further include manipulating at least a portion of the set of un-curated data based upon the data discrepancy to form a set of manipulated data. The method may further include comparing the set of manipulated data to a curation requirement threshold. The method may further include packaging, upon determining that the manipulated data meets the curation requirement threshold, at least a portion of the set of manipulated data as a set of curated data. The method may further include sending information indicative of the set of curated data to the user device in response to the data request.

A second embodiment of the invention is directed to a computerized method. The method may include receiving, from a user device, a data request corresponding to a person. The method may further include accessing a curation index to determine if there is indexed data at least partially responsive to the data request. The method may further include acquiring, from a data store, a set of un-curated data associated with the person and associated with at least a portion of the data request not determined to be in the curation index. The method may further include analyzing the set of un-curated data via an analysis engine to determine a data discrepancy. The method may further include manipulating at least a portion of the set of un-curated data based upon the data discrepancy to form a set of manipulated data. The method may further include comparing the set of manipulated data to a curation requirement threshold. The method may further include packaging, upon determining that the manipulated data meets the curation requirement threshold, at least a portion of the set of manipulated data as a set of curated data. The method may further include updating the curation index so as to indicate the set of curated data. The method may further include sending information indicative of the set of curated data to the user device in response to the data request.

A third embodiment of the invention is directed to a system comprising a user computing device and a server. The user computing device is configured to receive user input, and send a data request indicative of the received user input. The server is configured to: receive, from the user computing device, a data request corresponding to a person; acquire, from a data store, a set of un-curated data associated with the person; analyze the set of un-curated data via an analysis engine to determine a data discrepancy; manipulate at least a portion of the set of un-curated data based upon the data discrepancy to form a set of manipulated data; compare the set of manipulated data to a curation requirement threshold; package, upon determining that the manipulated data meets the curation requirement threshold, at least a portion of the set of manipulated data as a set of curated data; and send information indicative of the set of curated data to the user device in response to the data request.

In another embodiment, one or more non-transitory computer-readable storage media are provided for storing computer instructions thereon for execution by one or more processors to perform a method, such as described herein.

In one embodiment, a computerized system is provided in an embodiment of the present invention. The system comprises one or more processors configured to implement a method, such as described herein.

BRIEF DESCRIPTION OF DRAWINGS

Illustrative embodiments of the present invention are described in detail below with reference to the attached drawing figures, and wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described. Further, it will be apparent from this Detailed Description that the technological solutions disclosed herein are only a portion of those provided by the present invention. As such, the technological problems, solutions, advances, and improvements expressly referenced and explained should not be construed in a way that would limit the benefits and application of embodiments of the present invention.

Big data is a key feature of healthcare today. Providers need tools that enable them to understand large amounts of disparate data that is typically stored in an disorganized or difficult to understand manner. Different systems inevitably use different standards or formats for their data. Thus, interoperability is a key priority for entities to ensure their systems can communicate with a variety of other systems that may utilize different standards and/or formats. For example, a primary care provider (PCP) may refer a patient to a specialist and, as a result, send the patient's records to the specialist. The specialist may pull information from the PCP file that may need to be interpreted, customized, and updated to meet the demands of the specialist. As another example, stored data may include errors, redundancies, and omissions that prevent the caregiver from having a correct understanding of a medical condition of the patient. Such discrepancies can lead to medical errors.

Figure 1:
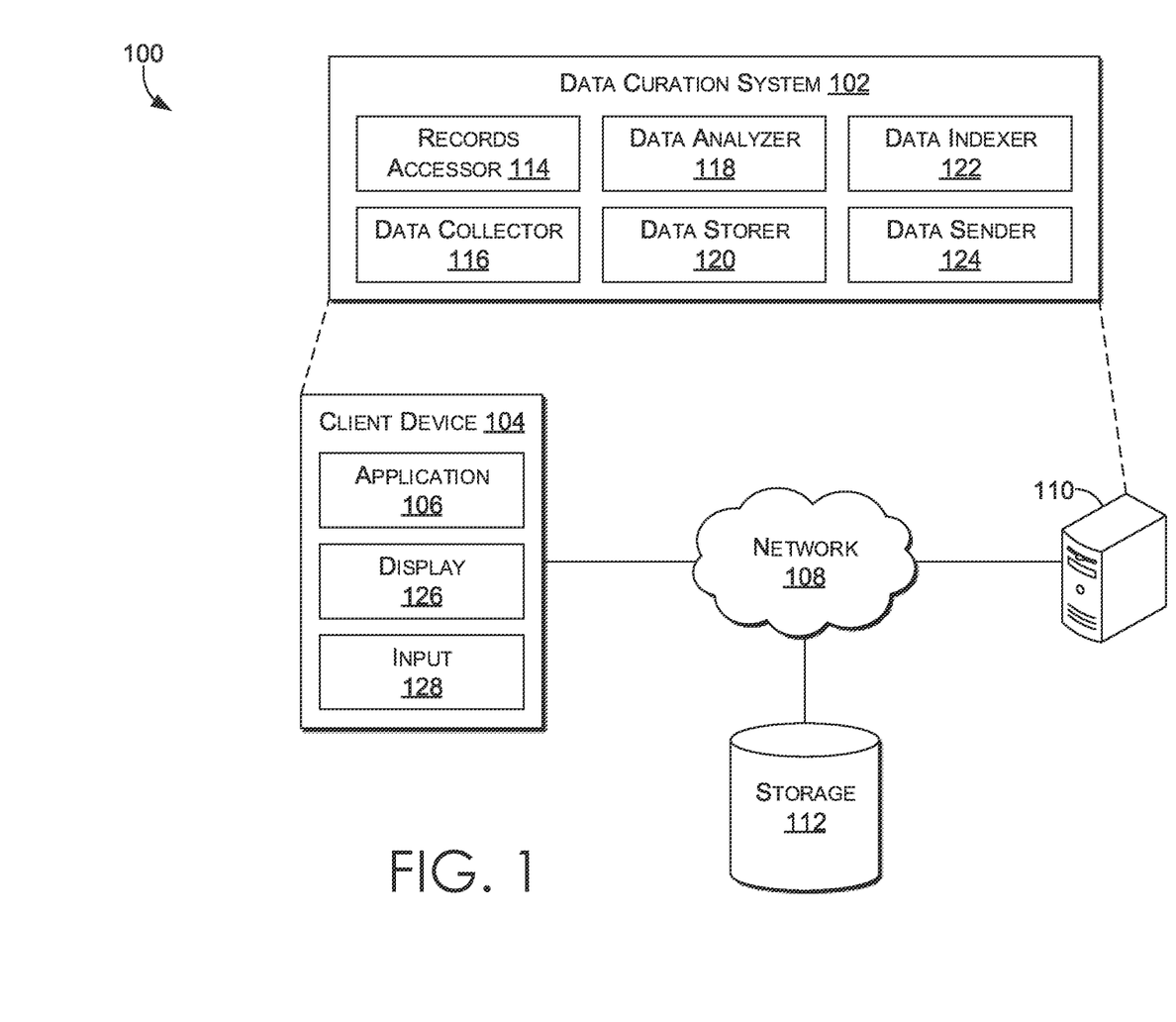
FIG. 1 depicts an example system in accordance with an embodiment of the present invention.

Having described an example aspect, further description is provided with reference to the drawings. Turning first to FIG. 1, the figure depicts a block diagram of example operating environment 100 suitable for use in implementing the described technology. As illustrated, environment 100 is suitable for implementing a data curation system 102.

It should be understood that operating environment 100 shown in FIG. 1 is an example of one suitable operating environment. Among other components not shown, operating environment 100 includes client device 104 having application 106. Client device 104 is illustrated communicating via network 108 to server 110 and storage 112. Server 110 is shown implementing data curation system 102. In other embodiments, all or a portion of the data curation system 102 may be implemented on the client device 104.

With specific reference to FIG. 1 generally, it should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether for the sake of clarity. It should also be understood that any number of client devices, servers, and other components may be employed within operating environment 100, and such aspects are intended to be within the scope of the present disclosure. Each of the components in FIG. 1 may comprise a single device or multiple devices cooperating in a distributed environment or in the cloud.

Further, many of the elements described herein are functional entities that may be implemented as discrete or distributed components or in conjunction with other components, and in any suitable combination and location. Various functions described herein as being performed by one or more entities may be carried out by hardware, firmware, software, or any combination thereof. For instance, some functions may be carried out by a processor executing instructions stored in memory, as will be further described with reference to FIG. 8.

Each of the components shown in FIG. 1, and within the figures generally, may be implemented via any type of computing device, such as one or more of computing device 800 described in connection to FIG. 8, for example. These components may communicate with each other via a network, such as network 108, which may be wired, wireless, or both. Network 108 can include multiple networks, or a network of networks, but is shown in simple form so as not to obscure aspects of the present disclosure. By way of example, network 108 can include one or more wide area networks (WANs), one or more local area networks (LANs), one or more public networks such as the Internet, or one or more private networks. Where network 108 includes a wireless telecommunications network, components such as a base station, a communications tower, or even access points (as well as other components) may provide wireless connectivity. Networking environments are commonplace in offices, enterprise-wide computer networks, intranets, and the Internet. Accordingly, network 108 is not described in significant detail.

Client devices, generally, such as client device 104, can be any type of computing device capable of being operated by a user, which may be any person or entity that provides or utilizes aspects of data curation system 102. In some implementations, client device 104 is the type of computing device described in relation to FIG. 8. For example, client device 104 may be embodied as a personal computer (PC), a laptop computer, a mobile device, a smartphone, a tablet computer, a smart watch, a wearable computer, a personal digital assistant (PDA), a global positioning system (GPS) or device, a video player, a handheld communications device, a gaming device or system, an entertainment system, a vehicle computer system, an embedded system controller, a remote control, an appliance, a consumer electronic device, a workstation, any combination of these delineated devices, or any other suitable device. Client device 104 can include a display device for displaying a graphical user interface. A suitable example is provided by I/O port 818 of FIG. 8.

Client device 104 can include one or more processors and one or more computer-readable media. The computer-readable media may include computer-readable instructions executable by the one or more processors. The instructions may be embodied by one or more applications, such as application 106, shown in FIG. 1. Application 106 is referred to as a single application for simplicity, but its functionality can be embodied by one or more applications in practice.

Application 106 is generally capable of facilitating the exchange of information between components of FIG. 1. For example, application 106 can facilitate receiving a request or other information from a user and receiving or executing instructions provided by data curation system 102. The application 106 may perform any or all of the steps of the data curation system 102. The application 106 may receive the requested curated data or other information for display from the server 110, storage 112, or other source.

In some implementations, application 106 comprises a web application, which can run in a web browser, and could be hosted at least partially on the server-side of operating environment 100. Application 106 can comprise a dedicated application, such as an application having analytics and display functionality. In some cases, application 106 is integrated into the operating system (e.g., as a service or program). It is contemplated that "application" be interpreted broadly. In some embodiments, application 106 is integrated with data curation system 102, which is illustrated as being executed by server 110.

Server 110 generally supports the data curation system 102. Server 110 includes one or more processors, and may comprise one or more non-transitory computer-readable media. The computer-readable media includes computer-readable instructions executable by the one or more processors. The instructions may optionally implement one or more components of data curation system 102. Though illustrated as distributed in nature, components of FIG. 1 can also be integrated in any fashion, including an aspect where server 110 is integrated with client device 104. The various method steps described herein may be performed by any combination of the client device 104, the server 110, or other computing devices.

Storage 112 generally stores information including data, computer instructions (e.g., software program instructions, routines, or services), or models used in embodiments of the described technologies. Although depicted as a database component, storage 112 may be embodied as one or more data stores or may be in the cloud. In an aspect, storage 112 may include electronic medical records stored as part of an EHR system.

As noted, server 110 can execute one or more functions of data curation system 102, which may include a records accessor 114, a data collector 116, a data analyzer 118, an data storer 120, a data indexer 122, and a data sender 124. In other embodiments, one or more of the functions may be performed on the client device 104 or some other computing device. In some embodiments, the records accessor 114 may be performed by the server 110 while the other discussed functions may be performed at the client device 104.

In general, the records accessor 114 may access, pull, retrieve, review, or otherwise obtain data from one or more electronic health records or other data source. The records accessor 114 obtains a set of result data. The result data may be indicative of results of one or more tests, labs, readings, results, or other information. The result data may include numerical values for the one or more results. The result data may also include identifying information for a certain patient. The result data may include a timestamp for the one or more results, such that the results may be plotted according to the timestamps. The timestamp may be indicative of a date and/or time in which the test was taken, the result obtained, the sensor was read, etc.

The raw data collections collected by the records accessor 114 may be stored in any system capable of storing, receiving, transmitting, or the like, records or any health-related data. Any one of the sources can be an electronic health record (EHR) server, a health information exchange (HIE), a patient portal, a government database, a pharmacy database, etc. The content available within these sources can include records of treatment events, medication history, diagnoses, problems, allergies, demographic attributes, summary of episode notes (SOEN), CDA (Clinical document architecture) documents, laboratory tests and/or results, time and data information, images, clinical notes, appointment notes, emergency contact information, clinical documentation of any kind, and any other health-related data, or any combination thereof for a plurality of individuals. Sources can be disparate sources or, in other words, may be associated with different entities (e.g., a first source may be associated with a hospital in Pennsylvania while second source may be associated with a pharmacy in Florida unrelated to the first source). Each of the sources can utilize different standards or formats within their databases (e.g., JSON, XML, YAML, HL7, CCDA, etc.). Furthermore, while the records accessor 114 may pull from a single source (e.g., a single databases) or from multiple data stores each associated with one or many different entities. One of skill in the art will understand the sources can take a variety of forms, be represented as multiple components, and communicate with any number of other sources.

In embodiments, the un-curated data collection may be retrieved from the storage 112 (e.g., one or more of the above discussed sources), client device 104, and/or a local sensor. The un-curated data may be pulled from an electronic health record, a set of current readings (e.g., from a currently monitored sensor), a local record, or other repository of information. The un-curated data may include a mixture of current and previous readings, such that both may be displayed together for providing context.

As an example field of use, some embodiments of the invention may be directed to electronic health records and the curation of data therefrom. In this example field of use, a first facility may be a hospital, a second facility may be a primary care facility, and the client device 104 may be smartphone having one or more health-related applications thereon. The first facility, being the hospital in this example, may have (or otherwise communicate with) the server 110 for storing electronic records generated, updated, or otherwise accessed in conjunction with medical services provided at the hospital. The second facility, being the primary care facility, may have (or otherwise communicate with) the server 110 for storing electronic records generated, updated, or otherwise access in conjunction with medical services provided at the primary care facility. The client electronic device 104 may generate, update, or otherwise interact with electronic records. As an example, the client electronic device 104 may record sensor readings, location information, interactions with an application, and/or other information. The various data being recorded from the various sources may include any of various errors, duplications, omissions, irrelevance, and the like (generally referred to as being un-curated). Embodiments of the invention curate this data to correct and select data for presentation.

A set of electronic records may be stored on one or more electronic devices. Following the example above, the server 110 may contain a first electronic record generated from the first facility, a second electronic record from the second facility, and a third electronic record from the client device 104. Each electronic record may be indicative of a patient, one or more clinical concepts, one or more caregivers, and other information. This data may be curated by various embodiments of the invention as discussed herein.

In order for a computerized system to organize source records (i.e., those records already present in a source system) and received records (i.e., those records received from disparate systems) and understand the information stored in electronic records, the data collector 116 can pull data from the accessed/received records. The data collector 116 may combine at least a portion of one or more electronic records to form the raw data collection. The data collector 116 may apply rules to determine what data from the accessed records to form the raw data collection. A separate rule can be used to evaluate each possible combination of variables and values for each variable that may be present in the accessed record and may be associated with the received request. In some embodiments, the data collector 116 may be referred to as a pre-processor.

The data analyzer 118 comprises instructions to perform iterative curation processes, as described herein. In particular, and as described further herein, the data analyzer 118 can receive the raw data collection from the data collector 116 based upon the one or more electronic records from the records accessor 114 perform iterative analyses to identify curatable data and to curate that data.

Initially, data from disparate sources can be received by the records accessor 114 and pre-processed by the data collector through BULK API 116, prior to communication to the data analyzer 118. The data analyzer 118 may consumes and/or output data in a particular format. In embodiments, the data analyzer consumes data in FHIR format. The data collected can be in any format and needs to be transformed to FHIR format to be used by the data analyzer 118. To do this, the data collector 116 identifies one or more parameters of the received data. In embodiments, two parameters that can be identified are the coding system (e.g., RXNORM, CVX, etc.) and the type (e.g., codeable concept or free text).

The data storer 120 may store the curated data, such as locally and/or in the storage 112 or in some other data store. In some embodiments, the curated data may be stored in a transitory memory for communication to the client device 104 before deletion. In other embodiments, the curated data may be stored in a non-transitory computer readable storage medium (such as storage 112 or other storage local or remote from the server 110). In these embodiments, the data storer 120 may keep a permanent or semi-permanent copy of the curated data so as to allow for the curated data to be retrieved for the current and/or future requests. For example, if the patient moves to a new caregiver, the new caregiver may be able to access the curated data on a new computing device. Similarly, if the patient returns at a future date for treatment, the caregiver may be able to recall the previously curated data (which may include updates or additions to that original curated data).

The data indexer 122 may create and/or update an index for the curated data. The index is a searchable record of what data and/or what patient have curated data stored by the data storer 120, as well as information on where to find such information. The index may be consulted by the data curation system 102 to determine whether all or a portion of the request can be performed with previously curated data. The index provides a reference to the data that was (or is, or will be) stored by the data storer 120). The data sender 124 may send the curated data to the client device 104 or to another computer or system. The data sender may package and/or encrypt the curated data for transfer. The data sender may include metadata about the curated data, which may include one or more sources, patient identification information, decryption information, and other information about the curated data.

The curated data, upon being received by the client device 104, may be shown on a graphical user interface (GUI) of a display 126 of the client device 104. The user may also select and/or manipulate the curated data via an input 128 of the client device 104. The input may include a touchscreen, a keyboard, a mouse, a button, or other type of device input. Based upon this display and/or interaction, new data requests may be generated and sent by the client device 104.

Figure 2:
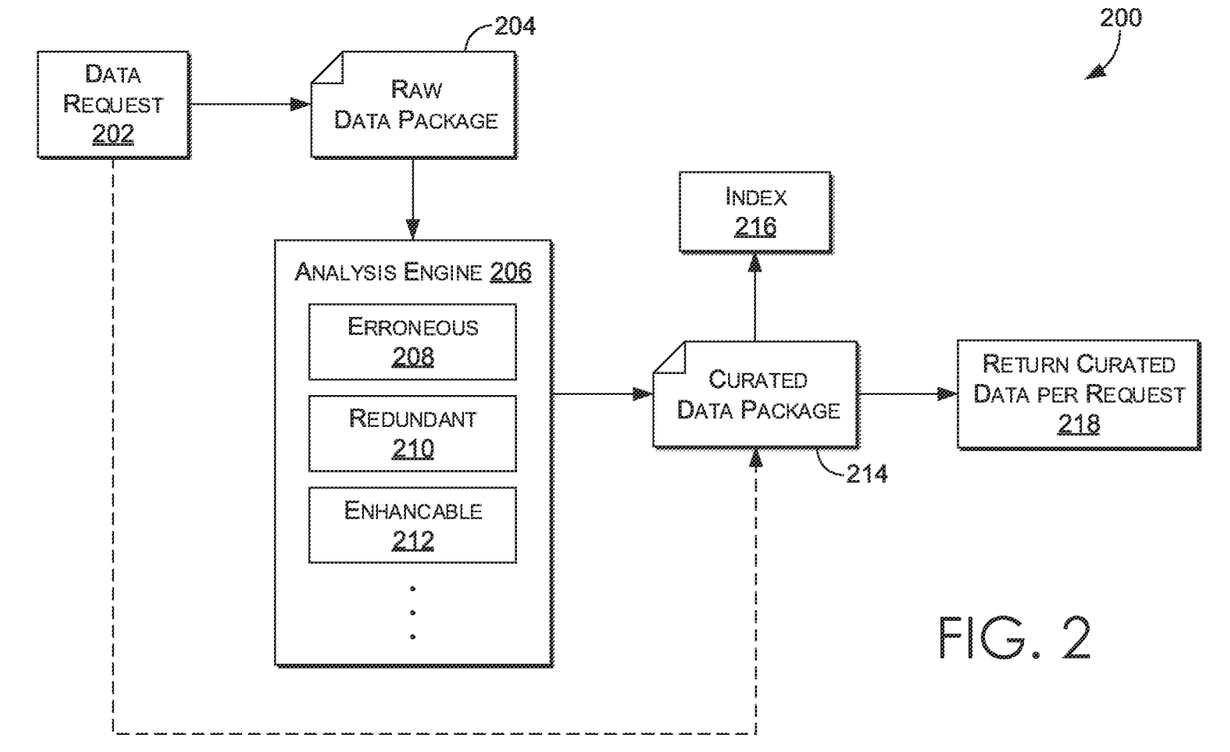
FIG. 2 depicts a block diagram of a data flow in accordance with an embodiment of the present invention.

Turning now to FIG. 2, steps of the data curation system 102 may be discussed, as data moves through the various components of the data curation system 102 and is modified and sent. A data request 202 is received and processed. The data request 202 is indicative one or more of a patient, a clinical condition, an event, a facility, a caregiver, The data request 202 is received from the client device 104 directly or indirectly. Based upon the data request 202, the system 102 may proceed to generate a curated data package 214 or access a previously created curated data package 214 to at least partially respond to the request.

A raw data package 204 is acquired in response to the request, which may include an EHR and/or other electronic records, and may include information from the request itself. The raw data package 204 is sent to an analysis engine 206 (such as the data analyzer 118 of FIG. 1) that analyzes the various aspects of the raw data package. The analysis engine 206 may identify erroneous data 208, redundant data 210, and/or enhance-able data 212. The analysis engine 206 can include an application programming interface (API) library that includes specifications for routines, data structures, object classes, and variables that support the interaction of the analysis engine architecture and the software framework of one or more disparate sources. These APIs can include configuration specifications for the system 100 such that the components therein can communicate with each other, as described herein.

For erroneous data 208, the analysis engine may locate and/or request corrections to the data. The requested corrections may be sent to the client device 104, the storage 112, or other computing device. The requested corrections may additionally or alternatively be identified from other information in the raw data package.

For redundant data 210, the analysis engine may weigh and rank the duplicative content such that the relevant content is written to the record appropriately and duplicate records are avoided. A duplicate, as used herein, refers generally to a record that is at least partially a copy of another record. In embodiments, a duplicate can be a record that has a probability/confidence level above a predetermined value to be a copy of another document or data set. The analysis engine may identify various parameters so that it is comparing like items and not items that are not related at all. Example parameters may include "system+codeable concept" or "system+free text" parameters in order to populate one or more groups of data. For example, different coding systems are used for different concepts: CVX is used to code vaccinations while RXNORM can be used to code medications. In processing an item, identification of the CVX system indicates an immunization concept. From that, either a codeable concept (e.g., numerical coding value: CVX 151) or free text (e.g., a textual name of the immunization: tetanus) can be identified. The "system+codeable concept" or "system+free text" parameters can be used to translate the data to FHIR-supported concepts. Put simply, if the coding system along with one or more of the codeable concept or free text is known, the information can be translated to FHIR standard. The translation can be done by the data collector 116, a separate translator service (not shown), a component of the data curation system 102, or the like. The translation can be completed using a translation map that maps various text and codes for a plurality of coding systems to FHIR standard terminology.

The analysis engine 204 may then output a curated data package 214. Alternatively, the analysis engine 206 may at least partially access a previously curated data package and may update or correct at least a portion thereof. The curated data package 214 may be indexed 216 and returned 218 per the request. The index 216 provides a searchable listing of the information and/or the associated patients which may be searched in future iterations. The returning 218 may be sent to the client device 104 for display, further analysis, or other purposes.

Figure 3:
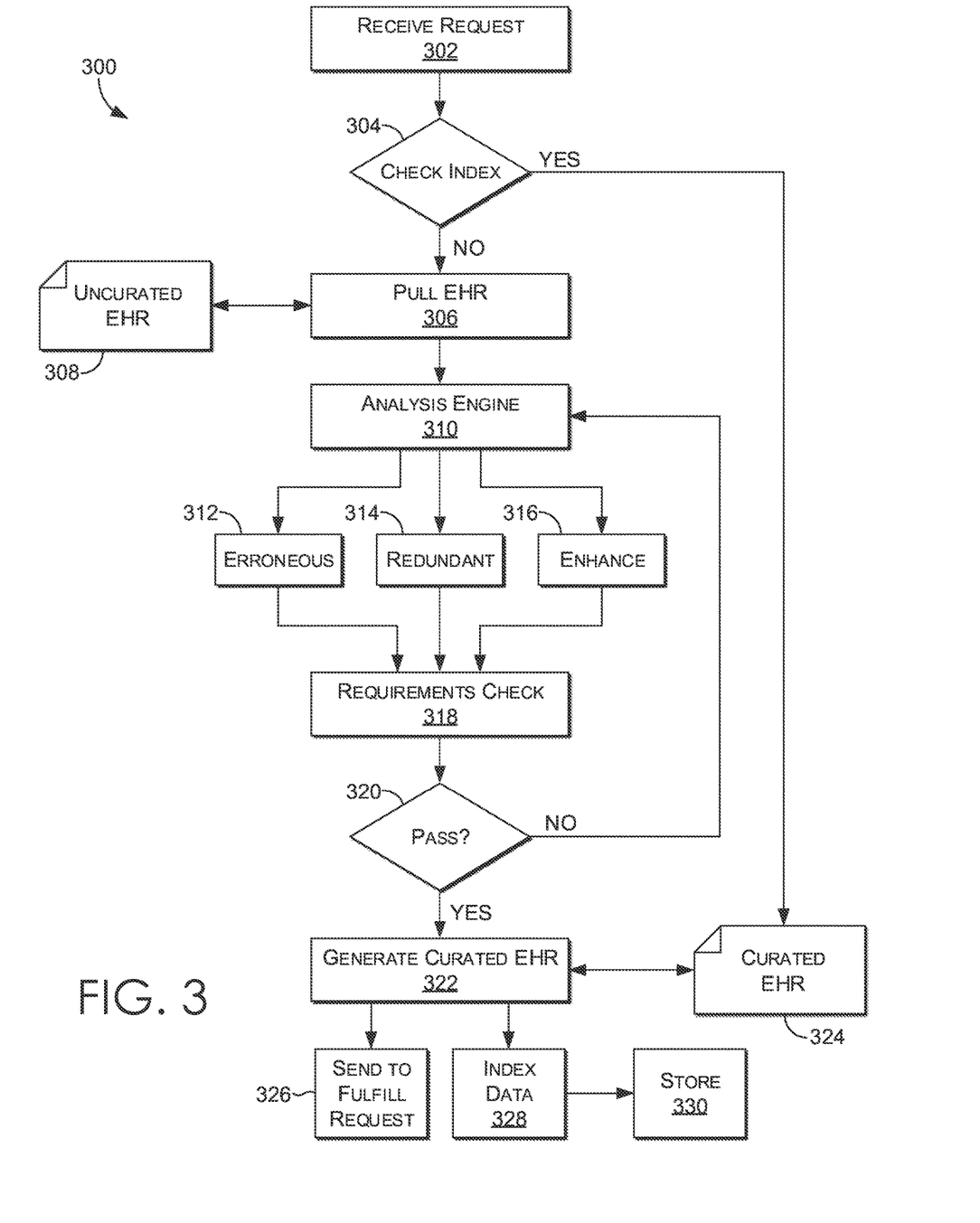
FIG. 3 depicts a flow diagram showing example steps of a method to curate data in response to a received request.

Turning now to FIG. 3, a method 300 of embodiments will now be discussed. In embodiments, this method 300 includes checking an index to determine if previously curated data is available so as to reduce the computational load in performing the method. The method may be performed by one or more processors (such as processor 814 of FIG. 8, a processor of the server 110, etc.). Generally, the method includes receiving a request, checking an index, generating a response to the request, and delivering the response.

In Step 302, the processor receives a request for data. A request can be obtained in any number of ways, some of which are described herein. As described with reference to FIG. 1, a request may be provided by an entity associated with the patient, such as a caregiver, through any of various computing devices. In one embodiment, a caregiver provides a request for data, including a set of patient parameters (e.g., via a graphical user interface). Such a request may be specific to an event data set (e.g., associated with a visit to that caregiver), specific for patient, specific to the patient or caregiver meeting some criteria (e.g., an amount of time has elapsed, or a new set of data is received).

In Step 304, the processor checks an index. If no index is available responsive to the request, or if the index provides no indication of relevant information already curated, the processor moves to Step 306. If an index is available and/or the index is indicative of at least some information associated with the request (e.g., associated with the patient), the processor may at least partially move to Step 324 discussed below.

In Step 306, the processor pulls an un-curated EHR 308 or other set of data to form an un-curated data collection. The processor may pull a subset of available data for the un-curated data collection based at least in part on the request for data.

In Step 310, the processor performs functions of an analysis engine 310, including identifying erroneous data 312, redundant data 314, and/or enhance-able data 316. The processor may manipulate at least a portion of the erroneous data 312, redundant data 314 and/or enhance-able data 316 so as to at least partially correct those discrepancies. The un-curated data collection, having at least of a portion thereof manipulated by the analysis engine 310 to correct one or more discrepancies may be referred to as a manipulated data set. The manipulated data set may be or may become the curated data set if it is sufficiently curated (as determined in Step 318 discussed below).

In Step 318, the processor performs a requirements check to determine if the data is sufficiently curated. In Step 320, the processor compares the requirements to a threshold to determine if the data passes the requirement for curation. If no, the processor may return to perform steps of the analysis engine in Step 310 or take other remedial actions. The threshold may be an indication of what data should be allowed for the set of curated data and what data should be excluded. In some embodiments, the threshold is indicative of how much uncorrected, redundant, and/or unenhanced data may be returned in response to the request. If the set of manipulated data fails to meet the threshold, any of various remedial actions may be taken by the processor. For example, as shown in FIG. 3, the processor may return to Step 310 and perform additional steps of the analysis engine. As another example, the processor may request additional information from the storage, from the user, or from some other sort so as to allow the analysis engine to sufficiently meet the threshold. If the threshold cannot be met, the system may return an error, request assistance from a human administrator, or provide the set of manipulated data with a warning indicative of why the data could not be sufficiently curated.

In Step 322, upon the data passing the requirements check, the processor will package the data as a set of curated data (such as a curated EHR 324). The processor may package, encrypt, or perform other functions to the set of curated data prior to sending.

Figure 6:
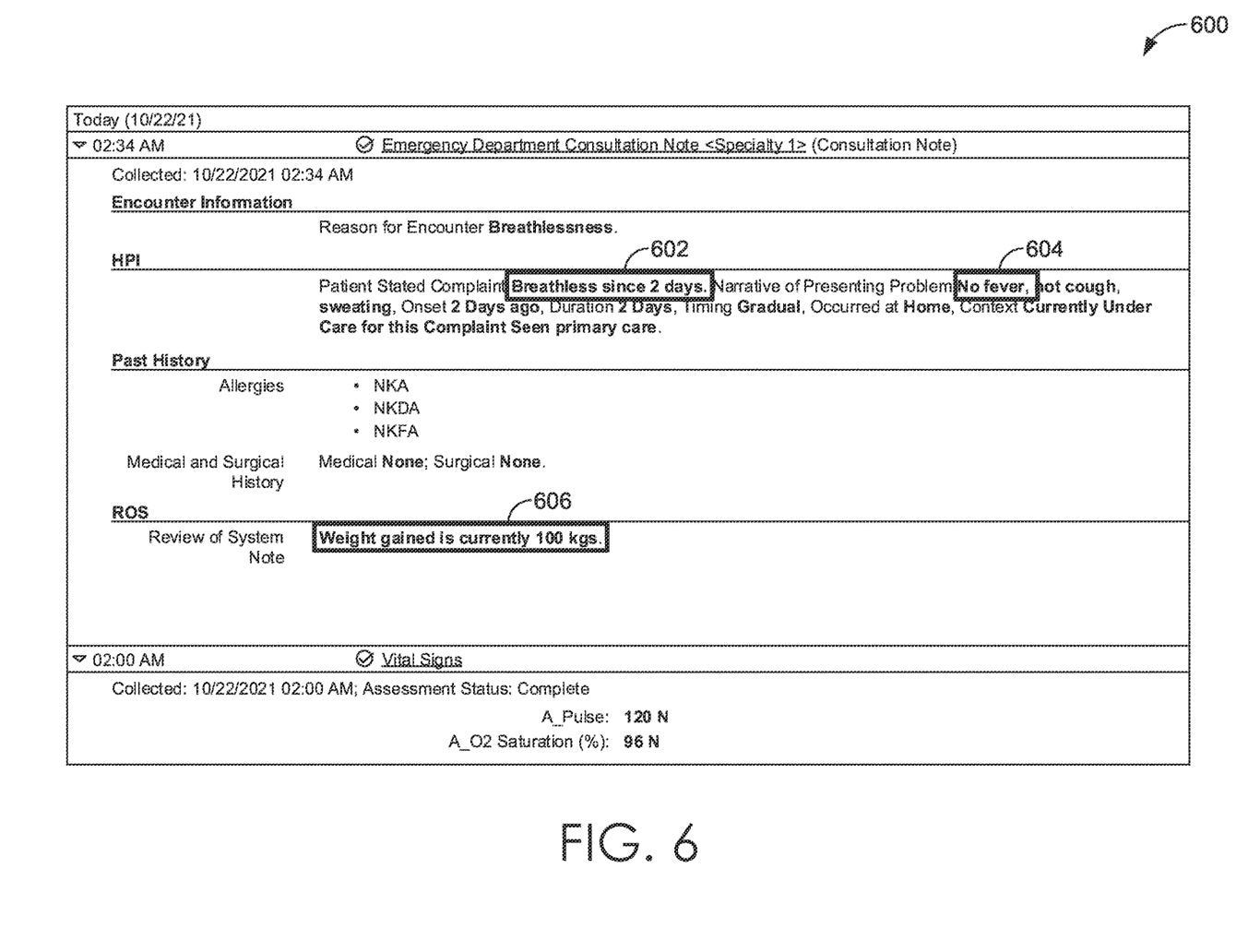
FIG. 6 depicts an graphical user interface configured to display curated data to the user in accordance with an embodiment of the present invention.

In Step 326, the processor sends at least a portion of the set of curated data (which may include at least a portion of the curated EHR 324) to fulfill the request. The recipient of the set of curated data (e.g., the client device 104 of FIG. 1) may then perform any of various functions with the set of curated data, as discussed below in reference to FIG. 4. For example, the recipient may display at least a portion of the curated data on a graphical user interface (GUI) such as shown in FIG. 6.

In Step 328, the processor indexes the curated data. Indexing may include creating, updating, modifying, or otherwise providing an indication of a location of the curated data. In Step 330, the processor stores the curated data, such that it can be later retrieved. The curated data may be later retrieved by reference to the index to provide a location or other information as to the curated data. In some embodiments, the index may point to the storage location of the curated data. In other embodiments, the index may provide an indication of how the raw data was manipulated into the curated data, such that the same or a similar function may be performed in future iterations of the method.

Figure 4:
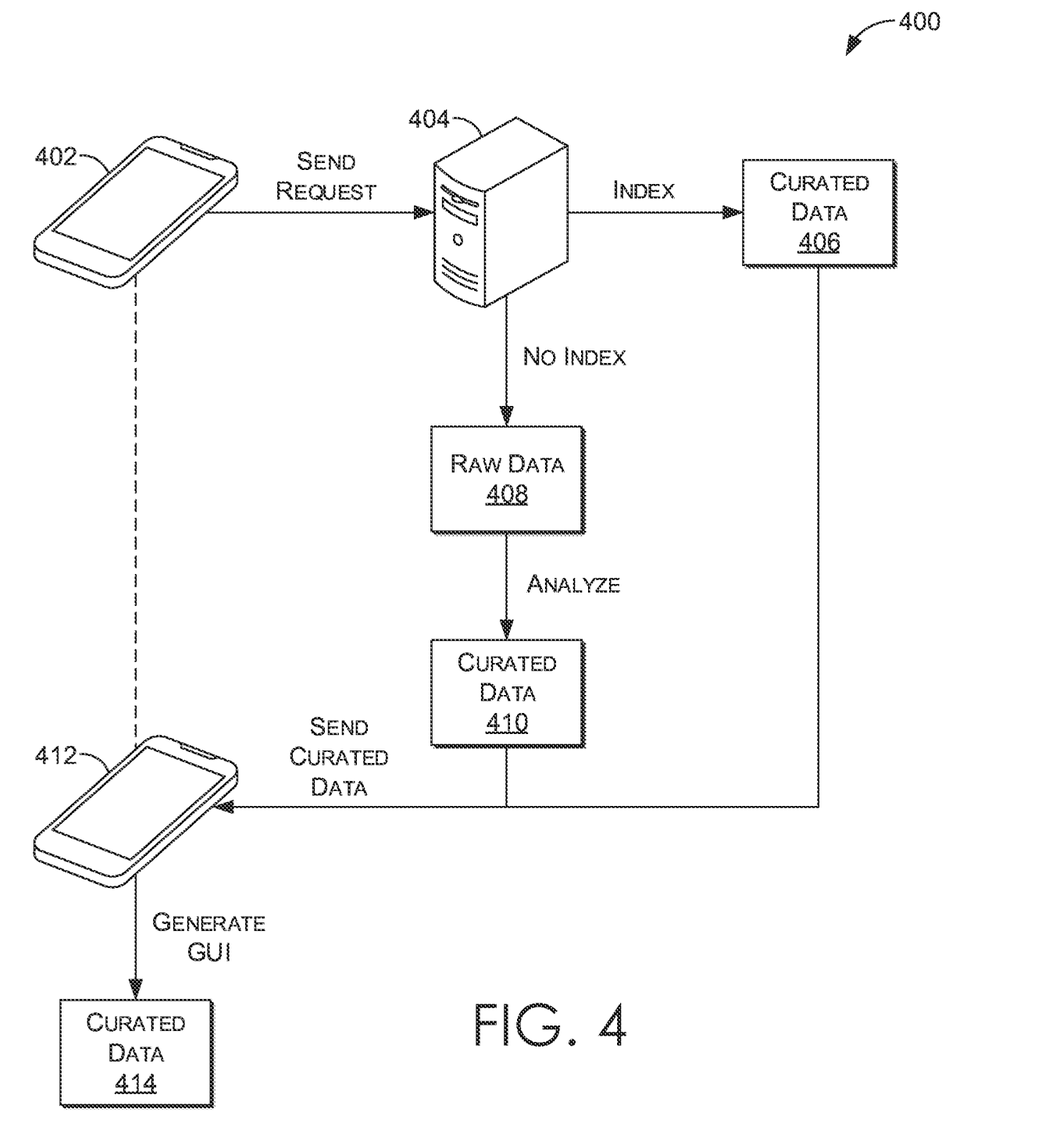
FIG. 4 is a flow diagram from the perspective of a user device that requests, receives, and displays curated data.

Turning now to FIG. 4, a method related to the user device will be discussed. In Step 402, the user device sends a request for data. In Step 404, the server checks the index to determine if there is curated data responsive to the request. If there is curated data responsive to the request, in Step 406 the server sends the curated data to the user device. If there is not curated data responsive to the request, in Step 408 the server retrieves raw data. In Step 410, the server curates the data as discussed herein. In Step 412, the user device receives the curated data from the server. In Step 414, the user device generates a graphical user interface (GUI) to display the curated data to the user.

Figure 5:
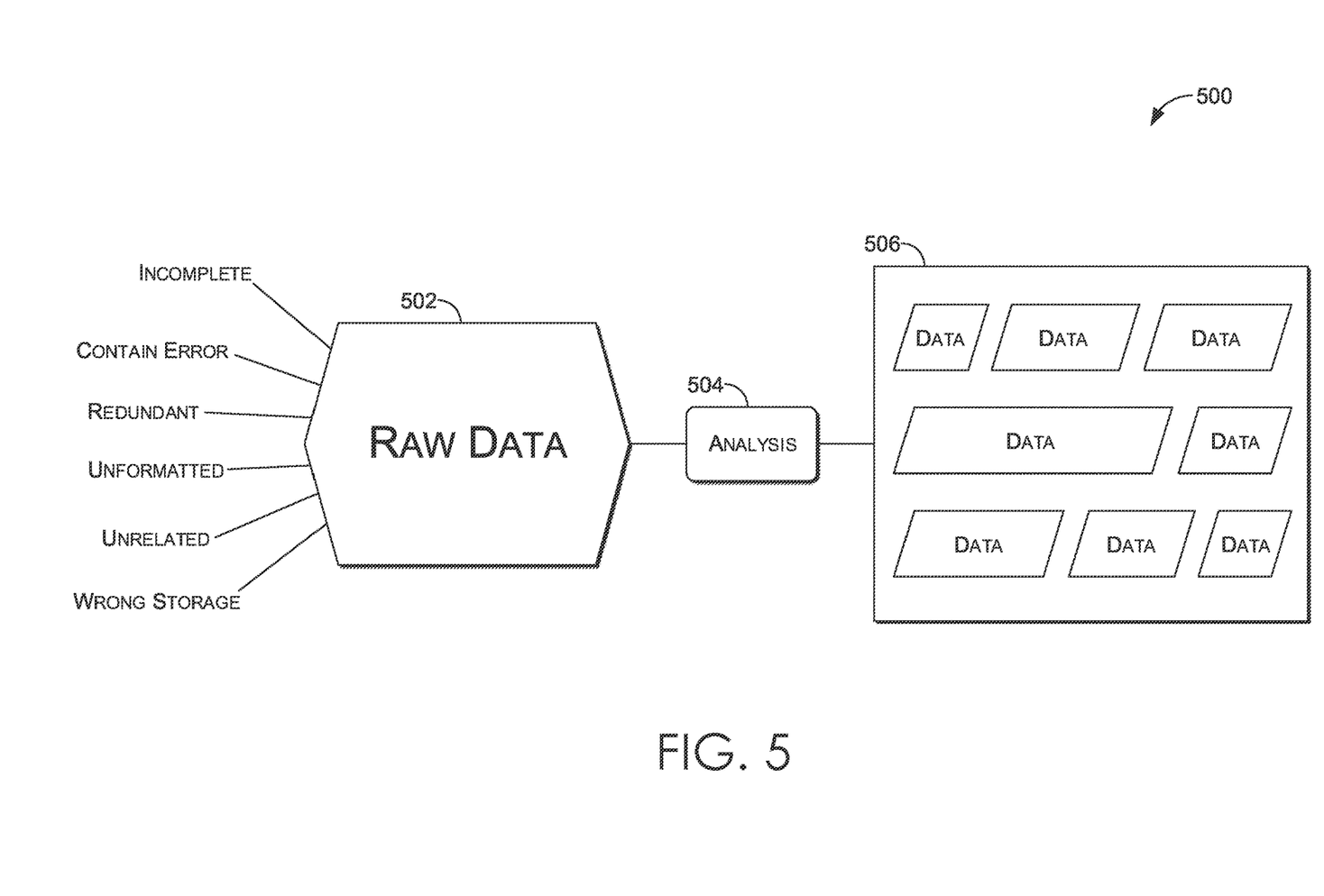
FIG. 5 is a diagram illustrating the curation process from raw data into a set of curated data.

FIG. 5 shows an example process flow depicting how data moves through some embodiments of the system, in accordance with embodiments described herein. Raw data 502 is collected for further analysis. The raw data is disorganized and may contain any of various un-curated features. As a first example, the raw data may include incomplete data (e.g., data that is missing that should be present). As a second example, raw data may include data that contains errors. As a third example, raw data may include data that is redundant. As a fourth example, raw data may include data that in unformatted or formatted in another format. As a fifth example, raw data may include data that is unrelated to the patient. As a sixth example, the raw data may include data that is stored incorrectly or in the wrong location.

The raw data 502 undergoes analysis 504 as discussed herein to create a set of curated data 506. The set of curated data is more complete, contains fewer errors, is less redundant, is correctly formatted, is related to the patient, and/or is stored correctly.

FIG. 6 shows an example GUI 600 configured to show the curated data to the end user. Three examples of curated data are shown in the GUI 600 to potential types of curation that may be used in various embodiments of the current disclosure.

In a first curated data set 602, the curation summarizes various other information from the set of raw data. Symptoms reported by the patient in a first encounter may be summarized for ease of referral by the user. In this example, the curated data is "Breathless since 2 days" as a summarized "Patient Stated Complaint." This allows the user to bypass otherwise disorganized information and instead view a summary of the entire encounter.

In a second curated data set 604, the curation analyzes and interprets various other information from the set of raw data. The curation takes raw data, such as a temperature reading of 97 degrees Fahrenheit, and provides a comment of "No fever" in the narrative. As such, the user need not interpret the raw data. This reduces the requirements on the end user.

In a third curated data set 606, the curation identifies an abnormality not directly in the raw data. The curation may identify data trends that may be relevant to the diagnosis of the patient, but which have not been independently identified. In this example, the curated data is "Weight gained is currently 100 kgs." This may be indicative of a weight gain of which the current user (e.g., a doctor currently seeing the patient) is not otherwise aware. This may be displayed on a "Review of System" label indicative that the determined alert was based upon a review of past EHR or other data.

Figure 7:
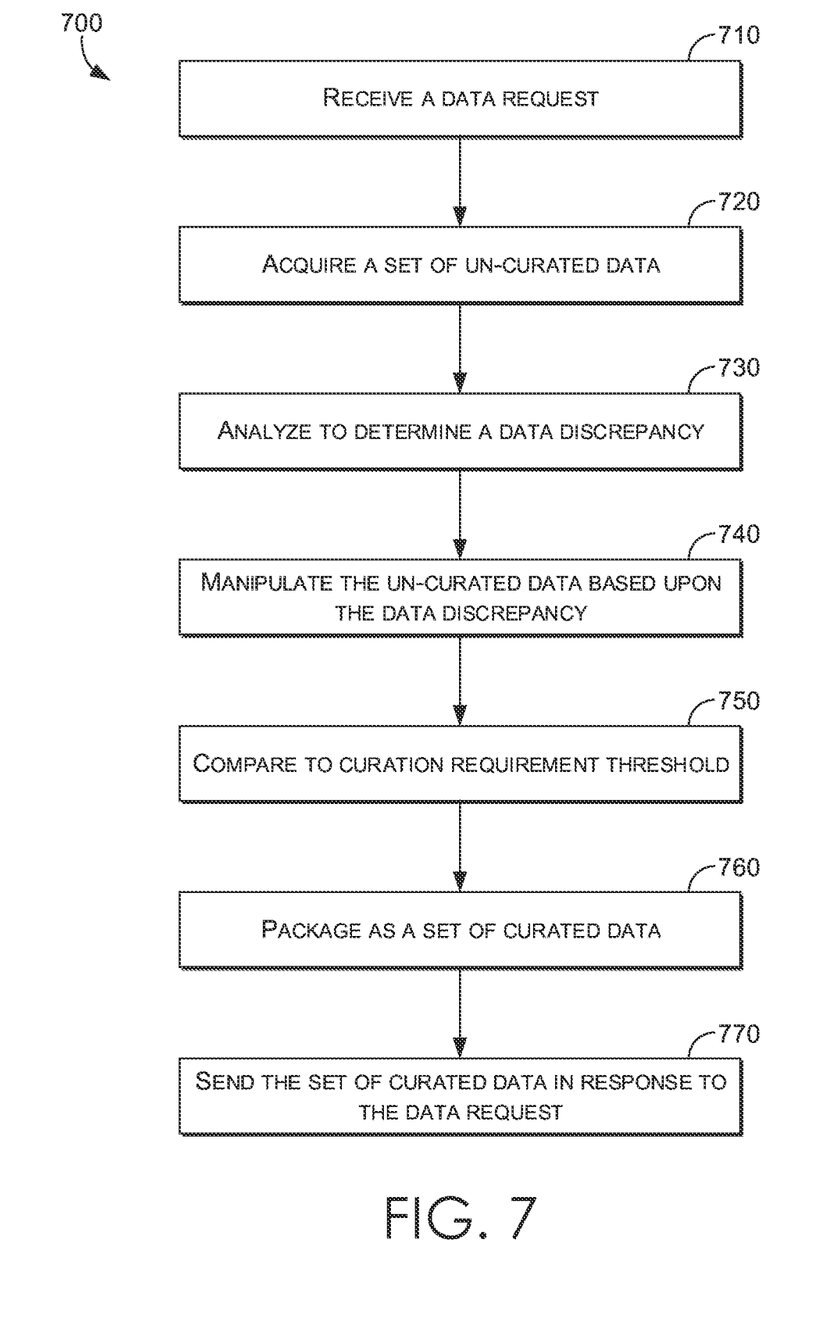
FIG. 7 depicts a method of curating data in response to a request, in accordance with an embodiment of the present invention.

Turning initially to FIG. 7, FIG. 7 illustrates method 700 for providing curated data in request to a response from a user device. At block 710, the method may include receiving a data request associated with a patient. The data request may request all available information for the patient or a subset of such information. At block 720, the method may include acquiring, from a data store, a set of un-curated data associated with the person. The un-curated data may be data stored in its native format in which it was received.

At block 730, the method may include analyzing the set of un-curated data via an analysis engine to determine a data discrepancy. The data discrepancy may be indicative of an error, a redundancy, a lack of information, or a lack of enhancement.

At block 740, the method may include manipulating at least a portion of the set of un-curated data based upon the data discrepancy to form a set of manipulated data. In the set of manipulated data the data discrepancy may be corrected, addressed, enhanced, corrected, or otherwise analyzed.

At block 750, the method may include comparing the set of manipulated data to a curation requirement threshold. The curation requirement threshold is indicative of whether the raw data has been sufficiently curated so as to meet the various criteria for curation.

At block 760, the method may include packaging, upon determining that the manipulated data meets the curation requirement threshold, at least a portion of the set of manipulated data as a set of curated data. Packaging may include organizing the data for display and/or encrypting the data for transmission.

At block 770, the method may include sending information indicative of the set of curated data to the user device in response to the data request. Upon receipt, the user device may display at least a portion of the curated data in the GUI for the user.

Hereinafter, an exemplary computing environment is described with regard to the systems, methods, and computer-media described hereinabove. Turning to FIG. 8, an exemplary computing environment is depicted, in accordance with an embodiment of the present invention. It will be understood by those of ordinary skill in the art that the exemplary computing environment 800 is just one example of a suitable computing environment and is not intended to limit the scope of use or functionality of the present invention. Similarly, the computing environment 800 should not be interpreted as imputing any dependency and/or any requirements with regard to each component and combination(s) of components illustrated in FIG. 8. It will be appreciated by those having ordinary skill in the art that the connections illustrated in FIG. 8 are also exemplary as other methods, hardware, software, and devices for establishing a communications link between the components, devices, systems, and entities, as shown in FIG. 8, may be utilized in implementation of the present invention. Although the connections are depicted using one or more solid lines, it will be understood by those having ordinary skill in the art that the exemplary connections of FIG. 8 may be hardwired or wireless, and may use intermediary components that have been omitted or not included in FIG. 8 for simplicity's sake. As such, the absence of components from FIG. 8 should be not be interpreted as limiting the present invention to exclude additional components and combination(s) of components. Moreover, though devices and components are represented in FIG. 8 as singular devices and components, it will be appreciated that some embodiments may include a plurality of the devices and components such that FIG. 8 should not be considered as limiting the number of a device or component.

Figure 8:
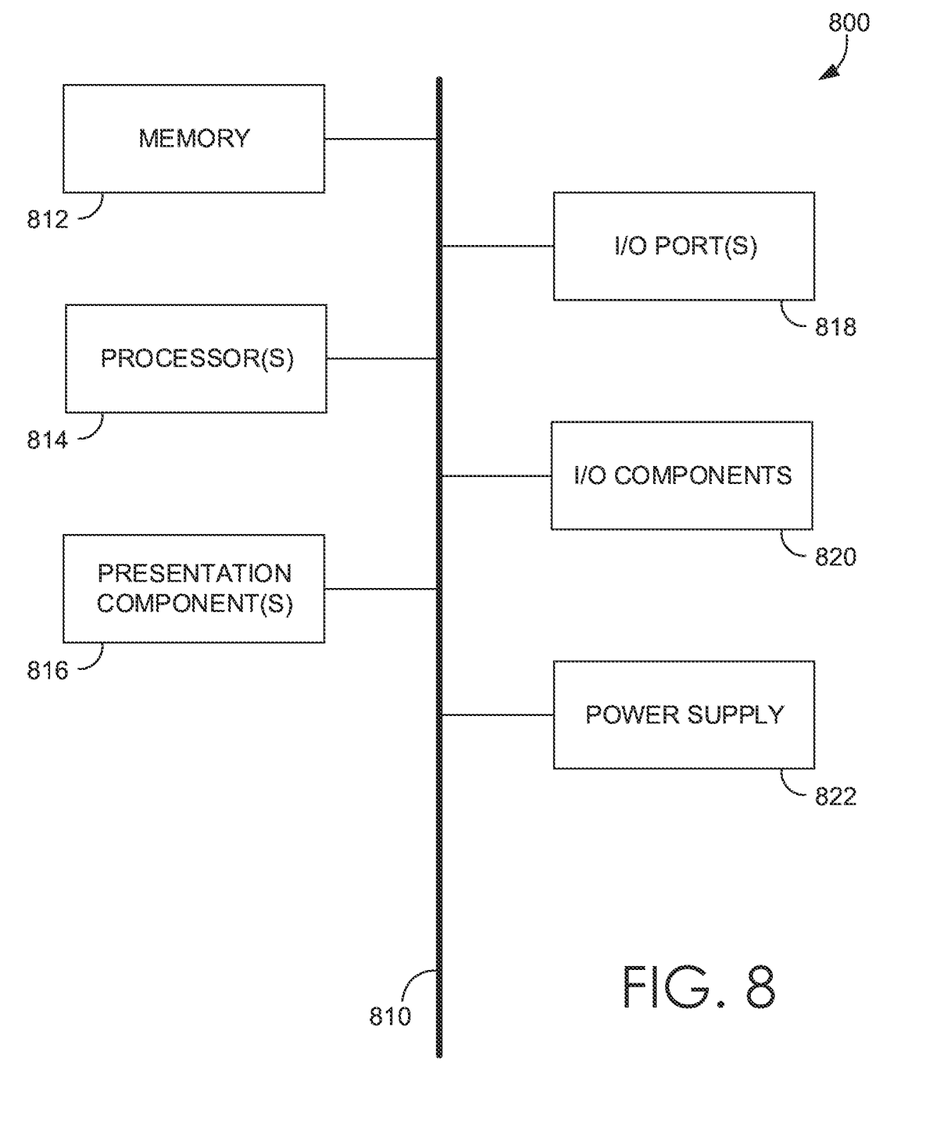
FIG. 8 depicts a block diagram of an exemplary computing environment suitable to implement embodiments of the present invention.

Continuing, the computing environment 800 of FIG. 8 is illustrated as being a distributed environment where components and devices may be remote from one another and may perform separate tasks. The components and devices may communicate with one another and may be linked to each other using a network 806. The network 806 may include wireless and/or physical (e.g., hardwired) connections. Exemplary networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. The network 806, generally, provides the components and devices access to the Internet and web-based applications.

The computing environment 800 comprises a computing device in the form of a server 804. Although illustrated as one component in FIG. 8, the present invention may utilize a plurality of local servers and/or remote servers in the computing environment 800. The server 802 may include components such as a processing unit, internal system memory, and a suitable system bus for coupling to various components, including a database or database cluster. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA®) local bus, and Peripheral Component Interconnect (PCI) bus, also known as Mezzanine bus.

The server 802 may include or may have access to computer-readable media. Computer-readable media can be any available media that may be accessed by server 802, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media, implemented in any method or technology for storage of information, such as computer-readable instructions, data structures, program modules, or other data. In this regard, computer storage media may include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 802. Computer storage media does not comprise signals per se.

Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also may be included within the scope of computer-readable media.

In embodiments, the server 802 uses logical connections to communicate with one or more remote computers 808 within the computing environment 800. In embodiments where the network 806 includes a wireless network, the server 802 may employ a modem to establish communications with the Internet, the server 802 may connect to the Internet using Wi-Fi or wireless access points, or the server may use a wireless network adapter to access the Internet. The server 802 engages in two-way communication with any or all of the components and devices illustrated in FIG. 8, using the network 806. Accordingly, the server 802 may send data to and receive data from the remote computers 808 over the network 806.

Although illustrated as a single device, the remote computers 808 may include multiple computing devices. In an embodiment having a distributed network, the remote computers 808 may be located at one or more different geographic locations. In an embodiment where the remote computers 808 is a plurality of computing devices, each of the plurality of computing devices may be located across various locations such as buildings in a campus, medical and research facilities at a medical complex, offices or "branches" of a banking/credit entity, or may be mobile devices that are wearable or carried by personnel, or attached to vehicles or trackable items in a warehouse, for example.

In some embodiments, the remote computers 808 is physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. By way of example, a medical professional may include physicians; medical specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; veterinarians; students; and the like. In other embodiments, the remote computers 808 may be physically located in a non-medical setting, such as a packing and shipping facility or deployed within a fleet of delivery or courier vehicles.

Continuing, the computing environment 800 includes a data store 804. Although shown as a single component, the data store 804 may be implemented using multiple data stores that are communicatively coupled to one another, independent of the geographic or physical location of a memory device. Exemplary data stores may store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. Exemplary data stores may also store data in the form of electronic records, for example, electronic medical records of patients, transaction records, billing records, task and workflow records, chronological event records, and the like.

Generally, the data store 804 includes physical memory that is configured to store information encoded in data. For example, the data store 804 may provide storage for computer-readable instructions, computer-executable instructions, data structures, data arrays, computer programs, applications, and other data that supports the functions and action to be undertaken using the computing environment 800 and components shown in exemplary FIG. 8.

In a computing environment having distributed components that are communicatively coupled via the network 806, program modules may be located in local and/or remote computer storage media including, for example only, memory storage devices. Embodiments of the present invention may be described in the context of computer-executable instructions, such as program modules, being executed by a computing device. Program modules may include, but are not limited to, routines, programs, objects, components, and data structures that perform particular tasks or implement particular abstract data types. In embodiments, the server 802 may access, retrieve, communicate, receive, and update information stored in the data store 804, including program modules. Accordingly, the server 802 may execute, using a processor, computer instructions stored in the data store 804 in order to perform embodiments described herein.

Although internal components of the devices in FIG. 8, such as the server 802, are not illustrated, those of ordinary skill in the art will appreciate that internal components and their interconnection are present in the devices of FIG. 8. Accordingly, additional details concerning the internal construction device are not further disclosed herein.

Also, the present invention has been described in relation to particular embodiments, which are intended in all respects to be illustrative rather than restrictive. Thus the present invention is not limited to these embodiments, but variations and modifications may be made without departing from the scope of the present invention.

What is claimed is:

1. A computerized method comprising:
   receiving, at a data curation system, a curation request to generate a curated dataset, wherein the curation request comprises (a) a first curation requirement for identifying and correcting one or more data discrepancies in un-curated data and (b) a second curation requirement for generating one or more enhancements to the un-curated data;
   accessing, by the data curation system, a plurality of electronic record sources;
   identifying, by the data curation system, a plurality of electronic records stored in the plurality of electronic record sources;
   acquiring, by the data curation system, a set of un-curated data from the plurality of electronic records;
   executing, by the data curation system, an iterative process to generate the curated dataset from the set of un-curated data, wherein executing the iterative process comprises executing a first set of one or more iterations of the iterative process corresponding to the first curation requirement, the first set of one or more iterations comprising:
      determining that the set of un-curated data comprises (a) a first subset of un-curated data from a first electronic record source, of the plurality of electronic record sources, configured according to a first coding system format and (b) a second subset of un-curated data from a second electronic record source, of the plurality of electronic record sources, configured according to a second coding system format,
      translating the first subset of un-curated data from the first coding system format to a third coding system format,
      translating the second subset of un-curated data from the second coding system format to the third coding system format,
      determining a data discrepancy between the first subset of un-curated data and the second subset of un-curated data that is revealed as a result of having translated the first subset of un-curated data and the second subset of un-curated data to the third coding system format enabling comparison of the un-curated data with the second subset of the un-curated data, wherein the data discrepancy comprises at least one of: an error or a redundancy,
      responsive to determining the data discrepancy, executing a manipulation upon at least a portion of the set of un-curated data to generate a set of manipulated data, wherein the manipulation comprises correcting the data discrepancy between the first subset of un-curated data and the second subset of un-curated data,
      determining that the set of manipulated data meets the first curation requirement based at least on the manipulation correcting the data discrepancy, wherein the first curation requirement comprises an amount of uncorrected and/or redundant data included in the set of manipulated data;
      responsive to determining that the set of manipulated data meets the first curation requirement:
         exiting the first set of one or more iterations of the iterative process and executing a second set of one or more iterations of the iterative process corresponding to the second curation requirement, the second set of one or more iterations comprising:
            generating a set of one or more enhancements to the set of manipulated data, wherein the set of one or more enhancements is based on at least one of: a first subset of manipulated data corresponding to the first subset of un-curated data, or a second subset of manipulated data corresponding to the second subset of un-curated data, and wherein generating the set of one or more enhancements comprises:
               generating, based on the set of manipulated data, a summary of one or more encounters with a patient,
               determining that the set of manipulated data meets the second curation requirement based at least on generating the summary of one or more encounters with the patient;
            responsive to determining that the set of manipulated data meets the second curation requirement:
               exiting the second set of one or more iterations of the iterative process and packaging at least a portion of the set of manipulated data as a set of curated data; and
   sending the set of curated data to a requesting device in response to the curation request.

2. The method of claim 1,
   wherein the data discrepancy is a redundancy,
   wherein executing the manipulation to generate the set of manipulated data comprises: deleting at least a portion of the first subset of un-curated data.

3. The method of claim 1,
   wherein the data discrepancy is an error,
   wherein executing the manipulation to generate the set of manipulated data comprises: correcting the error.

4. The method of claim 1, wherein acquiring the set of un-curated data comprises:
   forming a raw data package from at least a portion of the plurality of electronic records based at least in part on the curation request.

5. The method of claim 1, further comprising:
   updating a curation index indicative of the set of curated data so as to allow for later retrieval of the set of curated data.

6. The method of claim 5, further comprising:
   prior to generating the curated dataset:
   checking the curation index to determine whether at least a portion of the curation request can be fulfilled via previously curated data indicated on the curation index.

7. The method of claim 5, further comprising:
   storing at least a portion of the set of curated data in a non-transitory computer readable storage medium,
   wherein the curation index includes an address for the non-transitory computer readable storage medium wherein the set of curated data is stored.

8. A computerized method comprising:
   receiving, at a data curation system, a curation request to generate a curated dataset, wherein the curation request comprises (a) a first curation requirement for identifying and correcting one or more data discrepancies in un-curated data and (b) a second curation requirement for generating one or more enhancements to the un-curated data;
   accessing, by the data curation system, a plurality of electronic record sources;

identifying, by the data curation system, a plurality of electronic records stored in the plurality of electronic record sources;

acquiring, by the data curation system, a set of un-curated data from the plurality of electronic records;

executing, by the data curation system, an iterative process to generate the curated dataset from the set of un-curated data, wherein executing the iterative process comprises executing a first set of one or more iterations of the iterative process corresponding to the first curation requirement, the first set of one or more iterations comprising:

determining that the set of un-curated data comprises (a) a first subset of un-curated data from a first electronic record source, of the plurality of electronic record sources, configured according to a first coding system format and (b) a second subset of un-curated data from a second electronic record source, of the plurality of electronic record sources, configured according to a second coding system format,     translating the first subset of un-curated data from the first coding system format to a third coding system format,     translating the second subset of un-curated data from the second coding system format to the third coding system format,     determining a data discrepancy between the first subset of un-curated data and the second subset of un-curated data that is revealed as a result of having translated the first subset of un-curated data and the second subset of un-curated data to the third coding system format enabling comparison of the un-curated data with the second subset of the un-curated data, wherein the data discrepancy comprises at least one of: an error or a redundancy,     responsive to determining the data discrepancy, executing a manipulation upon at least a portion of the set of un-curated data to generate a set of manipulated data, wherein the manipulation comprises correcting the data discrepancy between the first subset of un-curated data and the second subset of un-curated data,     determining that the set of manipulated data meets the first curation requirement based at least on the manipulation correcting the data discrepancy, wherein the first curation requirement comprises an amount of uncorrected and/or redundant data included in the set of manipulated data;

responsive to determining that the set of manipulated data meets the first curation requirement:

exiting the first set of one or more iterations of the iterative process and executing a second set of one or more iterations of the iterative process corresponding to the second curation requirement, the second set of one or more iterations comprising:

generating a set of one or more enhancements to the set of manipulated data, wherein the set of one or more enhancements is based on at least one of: a first subset of manipulated data corresponding to the first subset of un-curated data, or a second subset of manipulated data corresponding to the second subset of un-curated data, and wherein generating the set of one or more enhancements comprises:

generating, based on the set of manipulated data, a summary of one or more encounters with a patient,             determining that the set of manipulated data meets the second curation requirement based at least on generating the summary of one or more encounters with the patient;

responsive to determining that the set of manipulated data meets the second curation requirement:

exiting the second set of one or more iterations of the iterative process and packaging at least a portion of the set of manipulated data as a set of curated data; and     sending the set of curated data to a requesting device in response to the curation request.

9. The method of claim 8, wherein the data discrepancy is a redundancy, wherein executing the manipulation to generate the set of manipulated data comprises: deleting at least a portion of the first subset of un-curated data.

10. The method of claim 8, wherein the data discrepancy is an error, wherein executing the manipulation to generate the set of manipulated data comprises: correcting the error.

11. The method of claim 8, wherein acquiring the set of un-curated data includes:

forming a raw data package from at least a portion of the plurality of electronic records based at least in part on the curation request.

12. The method of claim 8, further comprising:

updating a curation index indicative of the set of curated data so as to allow for later retrieval of the set of curated data;

storing at least a portion of the set of curated data in a non-transitory computer readable storage medium, wherein the curation index includes an address for the non-transitory computer readable storage medium wherein the set of curated data is stored.

13. A system comprising:

a computing device and a server, wherein the computing device is configured to:

receive an input; and send, to the server, a curation request corresponding to the input; and wherein the server is configured to:

receive, from the computing device, the curation request to generate a curated dataset, wherein the curation request comprises (a) a first curation requirement for identifying and correcting one or more data discrepancies in un-curated data and (b) a second curation requirement for generating one or more enhancements to the un-curated data;

access a plurality of electronic record sources;

identity a plurality of electronic records stored in the plurality of electronic record sources;

acquire, from a data store, a set of un-curated data from the plurality of electronic records;

executing an iterative process to generate the curated dataset from the set of un-curated data, wherein executing the iterative process comprises executing a first set of one or more iterations of the iterative process corresponding to the first curation requirement, the first set of one or more iterations comprising:

determining that the set of un-curated data comprises (a) a first subset of un-curated data from a first electronic record source, of the plurality of electronic record sources, configured according to a first coding system format and (b) a second subset of un-curated data from a second electronic record source, of the plurality of electronic record sources, configured according to a second coding system format, translating the first subset of un-curated data from the first coding system format to a third coding system format, translating the second subset of un-curated data from the second coding system format to the third coding system format, determining a data discrepancy between the first subset of un-curated data and the second subset of un-curated data that is revealed as a result of having translated the first subset of un-curated data and the second subset of un-curated data to the third coding system format enabling comparison of the un-curated data with the second subset of the un-curated data, wherein the data discrepancy comprises at least one of: an error or a redundancy, responsive to determining the data discrepancy, executing a manipulation upon at least a portion of the set of un-curated data to generate a set of manipulated data, wherein the manipulation comprises correcting the data discrepancy between the first subset of un-curated data and the second subset of un-curated data, determining that the set of manipulated data meets the first curation requirement based at least on the manipulation correcting the data discrepancy, wherein the first curation requirement comprises an amount of uncorrected and/or redundant data included in the set of manipulated data;

responsive to determining that the set of manipulated data meets the first curation requirement:

exiting the first set of one or more iterations of the iterative process and executing a second set of one or more iterations of the iterative process corresponding to the second curation requirement, the second set of one or more iterations comprising:

generating a set of one or more enhancements to the set of manipulated data, wherein the set of one or more enhancements is based on at least one of: a first subset of manipulated data corresponding to the first subset of un-curated data, or a second subset of manipulated data corresponding to the second subset of un-curated data, and wherein generating the set of one or more enhancements comprises:

generating, based on the set of manipulated data, a summary of one or more encounters with a patient, determining that the set of manipulated data meets the second curation requirement based at least on generating the summary of one or more encounters with the patient;

responsive to determining that the set of manipulated data meets the second curation requirement:

exiting the second set of one or more iterations of the iterative process and packaging at least a portion of the set of manipulated data as a set of curated data; and send the set of curated data to the computing device in response to the curation request.

14. The system of claim 13, wherein the data discrepancy comprises a first redundancy and a first error, wherein executing the manipulation to generate the set of manipulated data comprises: deleting at least a portion of the first subset of un-curated data to address the first redundancy, and correcting the first error.

15. The system of claim 13, wherein the server is further configured to:

form a raw data package from at least a portion of the plurality of electronic records based at least in part on the curation request.

16. The system of claim 13, wherein the server is further configured to:

update a curation index indicative of the set of curated data so as to allow for later retrieval of the set of curated data; and prior to generating the curated dataset:

check the curation index to determine whether at least a portion of the curation request can be fulfilled via previously curated data indicated on the curation index.

17. The system of claim 4, wherein the server is further configured to:

store at least a portion of the set of curated data in a non-transitory computer readable storage medium, wherein the curation index includes an address for the non-transitory computer readable storage medium wherein the set of curated data is stored.

18. The system of claim 13, wherein the computing device is further configured to:

display at least a portion of the curated dataset on a graphical user interface.

19. The computerized method of claim 1, further comprising, prior to generating the curated dataset:

checking an index to determine whether previously curated data is available.

20. The computerized method of claim 8, further comprising, prior to generating the curated dataset:

checking a curation index to determine whether previously curated data is available.

21. The system as in claim 17, the computing device being further configured to check an index to determine whether previously curated data is available.

22. The computerized method of claim 1, wherein generating the set of one or more enhancements comprises:

generating, based on the set of manipulated data, a set of one or more interpretations about the patient, and determining that the set of manipulated data meets the second curation requirement based at least on generating the set of one or more interpretations about the patient.

23. The computerized method of claim 1, wherein generating the set of one or more enhancements comprises:

identifying, based on the set of manipulated data, a set of one or more abnormalities that are relevant to a diagnosis for the patient, and determining that the set of manipulated data meets the second curation requirement based at least on generating the set of one or more abnormalities that are relevant to the diagnosis for the patient.

* * * * *